United States Patent [19]

Sherman et al.

[11] Patent Number: 5,510,561
[45] Date of Patent: Apr. 23, 1996

[54] HOMOGENOUS CATALYST AND PROCESSES FOR FLUID PHASE ALKYLATION

[75] Inventors: Larry G. Sherman; William A. Yuill, both of Edmond, Okla.

[73] Assignee: Kerr-McGee Chemical Corporation, Oklahoma City, Okla.

[21] Appl. No.: 399,405

[22] Filed: Mar. 6, 1995

Related U.S. Application Data

[63] Continuation of Ser. No. 94,520, Jul. 19, 1993, abandoned, which is a continuation-in-part of Ser. No. 993,601, Dec. 21, 1992, Pat. No. 5,406,018.

[51] Int. Cl.$^6$ ............................................. C07C 2/62
[52] U.S. Cl. .................... 585/734; 585/740; 585/741; 585/746; 585/747
[58] Field of Search ........................... 585/734, 740, 585/741, 746, 747

[56] References Cited

U.S. PATENT DOCUMENTS

| | | |
|---|---|---|
| 2,211,207 | 10/1938 | Ipatieff et al. . |
| 2,238,860 | 4/1941 | Kemp . |
| 2,249,366 | 7/1941 | Van Peski et al. . |
| 2,296,511 | 9/1942 | Frey et al. . |
| 2,301,615 | 11/1942 | Chenicek et al. . |
| 2,313,661 | 3/1943 | Montgomery . |
| 2,330,754 | 9/1943 | Skelton et al. . |
| 2,366,117 | 12/1944 | Leonard . |
| 2,401,859 | 6/1946 | Clarke . |
| 2,411,817 | 11/1946 | Thompson et al. . |
| 2,415,733 | 2/1947 | D'Ouville . |
| 2,428,417 | 10/1947 | Gray . |
| 2,674,637 | 4/1954 | Manne . |
| 2,816,150 | 12/1957 | Hepp . |
| 2,820,074 | 2/1958 | Pines . |
| 2,847,488 | 8/1958 | Boynton et al. . |
| 2,935,543 | 5/1960 | Smith . |
| 2,968,684 | 1/1961 | Hepp et al. . |
| 3,067,228 | 12/1962 | Evering et al. . |
| 3,114,785 | 12/1963 | Hervert et al. . |
| 3,345,428 | 10/1967 | McGrath et al. . |
| 3,470,264 | 9/1969 | Mayhue . |
| 3,476,825 | 11/1969 | Hutson, Jr. et al. . |
| 3,513,219 | 5/1970 | Mayhue . |
| 3,523,914 | 8/1970 | Mitsche et al. . |
| 3,531,542 | 9/1970 | Myers et al. . |
| 3,544,451 | 12/1970 | Mitsche et al. . |
| 3,636,127 | 1/1972 | Ranquist et al. . |
| 3,644,558 | 2/1972 | Wilke et al. . |
| 3,679,602 | 7/1972 | Pollitzer . |
| 3,706,814 | 12/1972 | Kirsch et al. . |
| 3,755,483 | 8/1973 | Burress . |
| 3,763,261 | 10/1973 | Sobel . |
| 3,786,107 | 1/1974 | Kuribayashi et al. . |
| 3,800,003 | 3/1974 | Sobel . |
| 3,836,594 | 9/1974 | Sampson et al. . |
| 3,862,257 | 1/1975 | Buben et al. . |
| 3,873,635 | 3/1975 | Prescott et al. . |
| 3,880,945 | 4/1975 | Kramer et al. . |
| 3,946,088 | 3/1976 | Leder et al. . |
| 3,960,764 | 6/1976 | Bernard et al. . |
| 4,065,516 | 12/1977 | Moser et al. . |
| 4,085,158 | 4/1978 | Dixon et al. . |
| 4,120,912 | 10/1978 | Hulme . |
| 4,138,444 | 2/1979 | Herbstman . |
| 4,218,569 | 8/1980 | Chase et al. . |
| 4,243,830 | 1/1981 | Carson . |
| 4,329,516 | 5/1982 | Al-Muddarris . |
| 4,405,500 | 9/1983 | Müller et al. . |
| 4,433,191 | 2/1984 | Elezar et al. . |
| 4,465,870 | 8/1984 | Herskovits . |
| 4,503,264 | 3/1985 | Al-Muddarris . |
| 4,513,153 | 4/1985 | Sandrin . |
| 4,581,474 | 4/1986 | Hutson, Jr. et al. . |
| 4,654,463 | 3/1987 | Sun et al. . |
| 4,754,078 | 6/1988 | Vora et al. . |
| 4,814,519 | 3/1989 | Harandi et al. . |
| 4,814,544 | 3/1989 | Olah . |
| 5,008,466 | 4/1991 | Schleppinghoff et al. . |
| 5,057,635 | 10/1991 | Garjda . |
| 5,103,059 | 4/1992 | Ihrman et al. . |
| 5,118,767 | 6/1992 | Job . |
| 5,120,897 | 6/1992 | Del Rossi et al. . |

OTHER PUBLICATIONS

A. K. Roebuck and B. L. Evering; "Isobutaine–Olefin Alkylation With In hibited Aluminum Chloride Catalysts;" *Ind. Eng. Chem. Prod. Res. Develop.*, vol. 9, No. 1, Mar. 1970; pp. 72–82.

George A. Olah, G. K. Surya Prakash, Jean Sonmer; "Superacids;" *Science*, vol. 206, No. 4414, Oct. 1979; pp. 13–20.

R. C. Alden, Fred E. Fey, Harold J. Hepp, Leo A. McReynolds; "Diisopropyl;" *The Oil and Gas Journal;* Feb. 9, 1946; pp. 70–107.

Lyle F. Albright; "Alkylation will be key process in reformulated gasoline era;" *Oil and Gas Journal.* Nov. 12, 1990; pp. 79–92.

Lyle F. Albright; "$H_2SO_4$ process compared, and new technologies revealed;" *Oil and Gas Journal*, Nov. 26, 1990; pp. 70–77.

*Primary Examiner*—Asok Pal
*Attorney, Agent, or Firm*—Herbert M. Hanegan; J. Rodgers Lunsford, III

[57] ABSTRACT

A discrete catalyst and processes for the alkylation of isoalkanes with alkenes under homogenous fluid conditions. The catalyst is formed by contacting, under fluid conditions, a homogenous fluid containing a paraffin hydrocarbon having from 4 to 12 carbon atoms with a Lewis acid/protic Bronsted acid pair to produce a discrete catalytic complex that is soluble in the fluid. The discrete catalyst is the reaction product of the acid pair and alkanes and includes hydrocarbon ligands of limited chain length rendering it soluble in the fluid. The catalyst is active for the alkylation of isoalkanes, under homogenous fluid conditions.

22 Claims, 2 Drawing Sheets

HOMOGENOUS CATALYST AND PROCESSES FOR FLUID PHASE ALKYLATION

This is a continuation, of application Ser. No. 08/094,520, filed Jul. 19, 1993, abandoned, which is a continuation-in-part of application Ser. No. 07/993,601, filed Dec. 21, 1992, now U.S. Pat. No. 5,406,018.

BACKGROUND OF THE INVENTION

1. Field of the Invention

The invention provides a homogenous reaction medium and process for using a homogenous Lewis acid-hydrocarbon complex catalyst for producing an alkylate product that is blendable into motor gasolines.

2. Description of the Related Art

Typical unleaded motor gasolines sold in various octane grades in the United States today are produced by blending together various component streams that are the end products of a variety of hydrocarbon refining processes. For example, a typical gasoline blend may contain, as its components, hydrocracker gasoline produced by catalytic hydrogenation in a "hydrocracking" unit, cracked gasolines produced by a fluidized catalytic cracker, reformate produced by the catalytic reformation of naphtha, isopentane produced by the catalytic isomerization of normal pentane, alkylate produced by the acid alkylation of isobutanes and olefins, normal butane produced from the distillation of crude oil or natural gas, etc. In order to produce gasolines having a specific octane rating and other specific properties, such as vapor pressure, the relative amounts of these component streams in the gasoline blend are adjusted. For example, if it is desired to produce a higher octane rated gasoline, then a larger proportion of the higher octane rated components will be added while lower octane components will be reduced or removed from the blend.

By way of background regarding octane ratings, it has long been recognized that highly branched hydrocarbons and aromatic hydrocarbons, such as benzene, toluene and xylene, have high octane numbers. This means that when these hydrocarbons are mixed with air under temperature and pressure conditions sufficient to permit complete vaporization, and the mixture is ignited, they burn with a steady rate of combustion and do not burn explosively. Explosive combustion or "knocking" will cause damage to internal combustion engines, if continued for any prolonged period of time. The oil refining industry has developed standards and methods for comparing the combustion of various hydrocarbons and blends of hydrocarbons. 2,2,4 trimethylpentane (commonly called "isooctane") is arbitrarily assigned an octane value of 100 and all other gasoline blending components are compared with this standard.

Alkylates are produced by an acid catalyzed reaction of an alkene with an isoalkane. The alkylate product stream comprises a mixture of multiply branched hydrocarbon compounds of increased carbon number. Highly branched hydrocarbon compounds, such as the trimethyl pentanes, are greatly valued as components for gasoline blends in order to increase the "octane" rating of the gasoline or otherwise modifying other properties of a gasoline fuel.

During the 1930's aircraft of increasing performance required the production of aviation fuels of increased performance, one important property of which was that of a higher octane rating. The highly branched hydrocarbon compounds of a high "octane" rating—such as 2,2,4 trimethylpentane, commonly known as "isooctane," and assigned a 100 octane rating—were not naturally abundant enough in crude oil to be produced in the quantities required for blending with gasoline to meet the quantity demands for high octane aviation fuel.

This gave rise to an intensive study during this early period of methods for producing highly branched alkanes in the gasoline fraction boiling range having high octane properties by reacting lower olefins with lower isoalkanes. There was little economic value in the 1930's-1940's for ethylene or lower isoalkanes, such as isobutane, which further provided incentive to the effort to convert them to highly valuable hydrocarbon products, such as high octane value blending compounds for gasoline fuels.

One method for preparing high octane value hydrocarbons which was developed during this period comprised exposing ethylene and isobutane to an acid-pair composition comprising a metal halide-type Lewis acid and a protic Bronsted acid—most commonly the Lewis acid being $AlCl_3$ and the protic Bronsted acid being HCl. Under such conditions the ethylene and isobutane react in the presence of the acid pair composition to form multiply branched hydrocarbon compounds of a $C_6$-$C_8$, and higher, carbon number, known as an "alkylate" product.

There are many reports in the literature of the 1930-1960 period on "alkylation" with a Lewis acid-Bronsted acid type of catalyst. See for example R. C. Alden et al., "Diisopropyl" *The Oil and Gas Journal*, pp. 70-73, 103-107 (Feb. 9, 1946); Clark Holloway et al., "Pilot Plant Production of 2,3-Dimethylbutane", *Industrial and Engineering Chemistry*, Vol. 38, No. 12, pp. 1231-1238 (Dec. 1946); R. B. Thompson et al., "Production of 2,3-Dimethylbutane by Alkylation", Vol. 40, No. 7, pp. 1265-1269 (July 1948); R. S. Manne, U.S. Pat. No. 2,674,637 (1954); and L. F. Mayhue, U.S. Pat. No. 3,470,264 (1969); and G. F. Prescott et al. U.S. Pat. No. 3,873,635 (1975). As was typical in all such processes, the acid-pair catalyst composition, an aluminum-chloride-hydrocarbon complex, formed as a "red oil" or sludge which was not miscible in the ethylene-isoalkane-alkylate hydrocarbon liquid phase. Typically the volume ratio of hydrocarbon feed to red oil catalyst volume ranged from about 1:1 to 1:3 and the reaction had to be performed under vigorous agitation conditions. Further, the activity of the acid-pair catalyst composition eroded over time and as the content of red oil or acid sludge increased. This made it necessary to continuously supply fresh makeup catalyst to the reaction zone while removing then disposing of spent catalyst sludge.

As time progressed, certain events occurred which displaced the acid pair method of alkylate production from commercial use. Non-alkylate octane booster additives were devised—such as the tetraethyl lead of "leaded" gasoline—and other methods were devised for production of alkylate streams, such as by HF and/or $H_2SO_4$ acid alkylation. Further, as the polymer industry began to develop and polyethylene came into great demand, ethylene achieved a high product value as a monomer and it became economically undesirable to utilize ethylene for alkylate production.

More recently, with the discovery of the health hazards associated with lead, tetraethyl lead has fallen into disrepute as an octane booster and production of "leaded" gasolines has been banned. This lead to the utilization of aromatic hydrocarbons as octane boosting gasoline additives—such as a combination of benzene-toluene-xylene—for the production of premium unleaded gasoline.

Commercial alkylation plants today may be divided into two categories, those that use sulfuric acid as the catalyst and others that use hydrogen fluoride (HF) as the catalyst for the alkylation reaction. While the sulfuric acid process is the older of the two, the relative importance of the hydrogen fluoride process has increased substantially in recent years so the HF-plants now produce about 47% of all alkylate. By the end of 1990 it was estimated that about 11% of the total gasoline pool consisted of alkylates produced by alkylating isobutane with $C_3$–$C_5$ olefins. Further, alkylation capacity in the United States totaled about 960,000 b/d of alkylate.

Both HF and sulfuric acid alkylation processes are postulated to proceed by the same overall reaction:

Thus, a postulated isobutyl cation reacts with an olefin (here 2-butene) to form a branched $C_8$ cation which in turn reacts with another isobutane molecule to form a neutral $C_8$ hydrocarbon (2,2,3 trimethylpentane) while regenerating another isobutyl cation. However, a number of competing side reactions also occur, the most troublesome of which produces polymerized olefins ("conjunct polymers" or "tars") which are more soluble in the acid phase than in the isobutane phase. The acid catalyst is not miscible with the hydrocarbon phase ( isobutane/2-butene/alkylate hydrocarbon) and the reaction is accomplished under vigorous agitation. The undesired polymerization reaction proceeds in the acid phase. In contrast, the desired alkylation reaction takes place predominantly at the acid/oil interface. To minimize formation of these polymers or tars and maximize alkylate yield, several operating variables are controlled: the acid:oil ratio in the reactor is minimized; the acid/oil interface is increased by high turbulence; olefin is diluted by a high isobutane: olefin ratio; and reactor temperature is maintained as low as possible.

During the alkylation of isobutane with $C_3$–$C_5$ olefins a portion of the acid catalyst is consumed. For instance, in sulfuric acid catalyzed alkylation, about 0.4–0.6 pounds of sulfuric acid is frequently required to produce about 1 gallon of alkylate, but much lower values, such as 0.1–0.25 pounds per gallon (ppg), can be realized at preferred conditions. Acid costs frequently account for about one third of the total operating costs of sulfuric acid catalyzed alkylation units.

In hydrogen fluoride catalyzed alkylation, HF consumption is often in the range of 0.08–0.25 ppg and regeneration of used HF is relatively easy and cheap. Further, since most of the HF is recovered and recycled, the amount of makeup HF required is small, usually about 0.15–0.2 pounds/bbl of alkylate. However, the conjunct polymers produced with HF alkylation may contain some residual HF and therefore pose a problem of environmentally acceptable disposal.

It now appears that the aromatic hydrocarbon octane boosters produce health hazards, such as being possibly carcinogens, as well as being contributors to ozone formation. The phaseout of aromatics as octane boosters will greatly increase the demand for high octane value alkylates, with their present day method for production giving rise to other concerns.

Aside from the problem of safely disposing of conjunct polymers produced in HF alkylation units, there is also growing public concern about the safety of HF alkylation units. When HF is released into the atmosphere, it forms a fine aerosol which appears to remain at ground level and is then transported by wind. In the event of a release of HF into the air, a concentration in the range of about 2–10 ppm causes irritation of the eyes, skin and nasal passages. Concentrations of about 20 ppm result in immediate danger to life and health. As a result of the hazards posed by inadvertent release of HF from HF alkylation plants, there is a need to develop other technologies for producing alkylate that do not have these attendant risks.

In A. K. Roebuck et al, "Isobutane-Olefin Alkylation With Inhibited Aluminum Chloride Catalyst," *Ind. Eng. Chem. Prod. Res. Develop.*, Vol. 9. No. 1 (March 1970) a renewed focus was given to an aluminum chloride type of catalyst which would dissolve more isobutane, to minimize production of heavy end products compared to HF or $H_2SO_4$ alkylation procedures, while also minimizing non-favored by-product as is typical with $AlCl_3$ based catalyst. An aluminum chloride-ether complex catalyst is described, which in conjunction with various inhibitors, appears capable of giving the desired results under certain conditions. Again, as typical with an aluminum chloride type catalyst, the catalyst phase is not miscible with the hydrocarbon phase, and the reaction medium is a non-homogeneous emulsion produced by vigorous agitation.

There exists a need for a high octane gasoline blending component which is not hazardous to health or the environment to replace aromatic components in the gasoline pool. While this need may be fulfilled by alkylate blending components, there yet exists a need for an alkylation process that is free of the perceived risks to human health and life associated with the use of the HF alkylation process, the tar disposal problem posed by both the sulfuric acid and the HF alkylation processes and the red oil problems associated with the use of an $AlCl_3$ type catalyst. Further, it is desirable to develop a process of alkylation that utilizes less catalyst in the reactors and held in inventory.

SUMMARY OF THE INVENTION

The invention provides for the formation of a homogeneous reaction medium containing a dissolved catalyst and a process for the alkylation of isoalkanes with olefins within the homogeneous reaction medium. The isoalkanes to be alkylated have from about 4 to about 12 carbon atoms.

The process utilizing this homogeneous medium is carried out at fluid conditions wherein the catalyst is dissolved in a paraffinic hydrocarbon preferably the isoalkane to be alkylated. As a result of the homogenous phase created, the alkylation reaction proceeds rapidly at temperatures of at least about 50° F. (10° C.) with high selectivity and at high conversion in the presence of a Lewis acid catalyst complex which is in solution in the medium in amounts which provide a concentration of Lewis acid of from about $3 \times 10^{-3}$ to about $20 \times 10^{-3}$ millimoles of dissolved Lewis acid per gram of medium. With respect to a preferred Lewis acid, an aluminum chloride, the catalyst complex is in solution in amounts from about 80 to about 550 wppm of aluminum. The process minimizes the production of conjunct polymers and undesirable or toxic waste products that pose problems with respect to environmentally safe disposal. Further, the process of this invention generally does not utilize hydrofluoric acid, in the manner and quantity in which it is used in the hydrofluoric alkylation processes, thereby eliminating the potential risk to human health by eliminating the risk of the formation of a hydrofluoric acid aerosol in the event of an unintended partial loss of the reactor contents.

The catalyst composition comprises a metal halide-type Lewis acid and a protic Bronsted acid as an integral part of the Lewis acid-hydrocarbon complex catalyst. It is desirable that the protic acid have an anion corresponding to the anionic component of the Lewis acid. The acid pair is associated to at least one hydrocarbon "chain" or "ligand" which is a hydrocarbyl radical having a formula $C_nH_{2n+1}$ wherein n is at most about 12, or which is an ether. The Lewis acid most preferred for formation of the catalyst is a di or trichloride of aluminum.

The invention comprises the formation of a homogenous reaction medium containing a Lewis acid-hydrocarbon complex catalyst dissolved in a paraffinic hydrocarbon and use of the homogeneous reaction medium containing the dissolved catalyst to promote the reaction of isoalkanes with olefins under homogeneous fluid conditions to produce an alkylate product stream. The homogeneous reaction medium containing dissolved catalyst can be produced as a liquid phase solution and employed in such fluid state to catalyze the desired reaction—alkylation—under homogeneous liquid phase conditions.

Upon completion of the desired reaction the separation of catalyst from the hydrocarbon content of the fluid medium may be readily accomplished. If reaction is performed under liquid phase conditions the hydrocarbon content of the medium may be separated from the catalyst by flashing or alternatively by subjecting the liquid medium to an absorbent for the catalyst. The recovered catalyst may be recycled for reuse with feeds of fresh makeup reagents to form fresh charges of a homogenous reaction medium for further reaction.

The catalyst composition comprises a hydrocarbon soluble complex which forms upon the interaction of a metal halide-type Lewis acid and a protic Bronsted acid with a paraffin hydrocarbon. Wherein alkylation is to be accomplished, the isoalkane reactant may be used as the fluid component of the medium.

Production of the homogeneous reaction medium containing dissolved catalyst can be accomplished in a variety of ways. The fluid component of the medium can be brought into contact with a source of solid Lewis acid simultaneously with contacting it with a Bronsted acid, then the fluid removed from further contact with the solid Lewis acid to produce a homogeneous fluid solution of the two components. More preferably, the fluid component of the medium is brought into then removed from contact with the solid Lewis acid before the Bronsted acid component is added to the fluid. Alternatively, a soluble catalyst can be produced by reacting a Lewis acid with an alkyl halide which at the temperature for isomerization or alkylation reaction decomposes into an alkene and a hydrogen halide acid.

DETAILED DESCRIPTION OF THE PREFERRED EMBODIMENTS

The invention provides a catalyst, a method for producing this catalyst, and processes for utilizing the catalyst in alkylation reactions conducted in a homogeneous reaction medium. The alkylation process combines isoalkanes having from 4 to 12 carbon atoms with olefins having from 2 to 9 carbon atoms.

The alkane serves a plurality of functions in the process of this invention. It is a reactant which undergoes the desired alkylation reactions, in the presence of the dissolved Lewis acid-hydrocarbon complex catalyst. However, a portion of the alkane also serves as a reagent in the formation of the dissolved catalyst complex which catalyzes the desired alkylation reactions. Further, the alkane also serves as a component of the fluid in which the catalyst complex is soluble. Thus, the alkane forms a part of the homogenous fluid medium wherein the reaction occurs by which the hydrocarbon reactant is reacted to produce a product hydrocarbon of a different molecular structure.

The Fluid of the Reaction Medium

In accordance with this invention, the desired reaction—alkylation—is carried out within a homogenous fluid medium. The fluid of the reaction medium may be a liquid hydrocarbon.

Liquid Phase Fluids

When liquid phase reaction conditions are selected for the practice of this process, the fluid for the reaction medium is preferably a liquified hydrocarbon which is also a reactant hydrocarbon in the process. For an alkylation reaction, the fluid of the reaction medium is preferably selected to be the isoalkane which is a reactant for the olefin reactant of the alkylation process. Again, in this case the isoalkane serves the function of a fluid for forming the homogenous reaction medium and also as a hydrocarbon reactant in that medium. In a preferred embodiment of a liquid phase alkylation reaction according to the invention, the fluid of the reaction medium is iso-butane.

In the case of a liquid phase reaction, the hydrocarbon selected as the fluid for the reaction medium will be maintained at a temperature below its critical temperature and under a pressure sufficient to maintain the hydrocarbon in the liquid state while forming the Lewis acid-hydrocarbon complex catalyst and while conducting the selected alkylation reactions.

For an alkylation reaction, the isoalkane which participates in the reaction is selected as the fluid for the homogeneous reaction medium. During the alkylation reaction the isoalkane should normally be present in the medium in a molar ratio to the olefin reactant of at least about 5:1 and greater. Accordingly, for liquid phase reaction the temperature of the isoalkane fluid should not exceed the critical temperature of the selected isoalkane. For alkylation isobutane is preferred, and the temperature of the fluid should not exceed 275° F. (135° C.).

For alkylation, the homogeneous reaction medium should be maintained at a temperature of at least about 50° F. (10° C.). For liquid phase alkylation wherein the catalyst is composed of an aluminum chloride, the fluid temperature should be maintained at a temperature of from about 50° to 220° F. (10° to 105° C.), more preferably from about 100° to 190° F. (38° to 83° C.), and most preferably from about 100° to 160° F. (38° to 71° C.).

In a liquid phase procedure, the reaction medium following reaction may be allowed to undergo flash evaporation to separate the hydrocarbon components from the catalyst complex. Again the unreacted excess isoalkane would be recovered. Alternatively the liquid medium containing unreacted alkane, and heavier alkylate product and catalyst, may be routed over a bed of absorbent for the catalyst to separate it from the alkylate product.

The Catalyst

The invention provides a homogeneous catalyst for the alkylation of olefins and alkanes. The catalyst comprises a Lewis acid of the metal halide-type, a protic Bronsted acid, and a hydrocarbon component. The Lewis acid-hydrocarbon complex catalyst is the product of reaction of at least (a) a Lewis acid of the formula $R_{(m-2-z)}MX_{2+z}$ wherein M is a Group 3a, 5a or 5b metal, X is a halide, R is a hydrocarbyl radical having 1 to 12 carbon atoms, "m" is an integer equal to the greatest oxidation state of M, and "z" is an integer of 0, 1 or m-2; (b) a hydrogen halide; and (c) an organic compound selected from (1) paraffins having 12 or fewer carbon atoms, or (2) olefins having 12 or fewer carbon atoms. All group references are with respect to the Periodic Table of Elements as published in *CRC Handbook of Chemistry and Physics*, 51st Edition (1970–71) published by The Chemical Rubber Co.

The useful Lewis acids include, for example, aluminum trihalides, alkylaluminum dihalides, gallium trihalides, alkylgallinium dihalides, boron trihalides, antimony pentahalides, tantalum pentahalides, and niobium pentahalides and the like. Of these, the fluorides of antimony, tantalum, niobium and boron are preferred while for aluminum and gallinium the chlorides are preferred. Most preferred as the Lewis acid component for the catalysts are chlorides of aluminum, such as aluminum trichloride, an alkylaluminum monochloride or alkylaluminum dichloride wherein the alkyl group has from 1 to 12 carbon atoms. Particularly preferred Lewis acids are aluminum trichloride and isobutylaluminum dichloride.

The Bronsted acids include the protic Bronsted acids that have an anion corresponding to the anion of the Lewis acid used. Thus, the Bronsted acid may be selected from hydrogen fluoride, hydrogen chloride, hydrogen bromide and hydrogen iodide. The preferred Bronsted acids are HCl and HBr. Since the most preferred Lewis acid is an aluminum chloride, the most preferred Bronsted acid is hydrogen chloride. The Bronsted acid may be supplied in the form of a Bronsted acid donor, namely a compound which at the temperature conditions for alkylation reactions decomposes to yield a Bronsted acid. Such Bronsted acid donors are alkyl chlorides like butyl chloride, which decomposes into butene and hydrogen chloride.

The organic compounds which may be utilized in forming the catalyst are the alkanes and/or olefins which are to be utilized as the reagents for the alkylation reaction.

The homogeneous medium containing the dissolved Lewis acid-hydrocarbon complex catalyst can be formed in a variety of ways. The fluid containing a hydrocarbon may be flowed through a bed of a solid Lewis acid, such as $AlCl_3$ to cause Lewis acid to dissolve in the fluid, then removed from further contact with the solid Lewis acid. Thereafter, a Bronsted acid or a Bronsted acid donor may be added to the fluid containing the dissolved Lewis acid. Wherein a Bronsted acid is added, the catalyst forms upon addition of the Bronsted acid. When a Bronsted acid donor, such as butyl chloride, is added, the catalyst complex forms when the fluid reaches a temperature at which the alkyl chloride ionizes in the presence of a Lewis acid.

It is preferred to solubilize the Lewis acid before adding the Bronsted acid or Bronsted acid donor. The preferred ratio of Bronsted acid or Bronsted acid donor to the Lewis acid halide is between 0.5 and 2.5 on a molar basis.

The catalyst when formed as a Lewis acid-hydrocarbon complex may be represented by the following formula:

$$[C_{at}]^+_a[R_{(m-2-z)}MX_{(2+z+a)}]^-$$

wherein "$C_{at}$" is a carbocation, R is a hydrocarbyl radical having from 3 to 12 carbon atoms, M is a group 3a, 5a, or 5b metal or metalloid, X is halide, "m" is an integer equal to the greatest oxidation state of M, "z" is 0, 1, or m-2, and "a" is a number greater than 0.5 and less than 2.5. Accordingly, when forming this catalyst the Bronsted acid halide (HX) should be added to the dissolved Lewis acid ($R_{m-2-z}MX_{2+z}$) in an amount that provides a molar ratio of Bronsted acid halide to Lewis acid of 1:2 to 5:2.

Formation of the Homogeneous Reaction Medium

The nature of the fluid phase as a liquid phase requires different methods for forming the homogeneous reaction medium. The content of catalyst dissolved in the medium, expressed as a Lewis acid content, may range from about 3.0 to about 30 millimoles of Lewis acid/1000 g of medium, preferably from about 3.0 to 22.5 millimoles/1000 g of medium, and more preferably from about 3.1 to about 20 millimoles/1000 g of medium.

Liquid Phase Operation

In liquid phase operation the catalyst may be conveniently prepared by dissolving the Lewis acid in a hydrocarbon liquid and thereafter, based upon the content of dissolved Lewis acid, adding appropriate quantities of Bronsted acid halide or Bronsted acid donor to the liquid. Alternatively the Bronsted acid halide or donor may be added to the alkylation reactor with the hydrocarbon liquid having the dissolved Lewis acid being separately added to the reactor. The catalyst forms in the homogenous mixture in the reactor.

However formed, the catalyst complex is dissolved in the homogeneous fluid medium in an amount that provides a catalyst concentration of from about 3.0 to about 20 millimoles per 1000 g of medium, measured as $MX_m$ where M is a Group 3a, 5a or 5b metal or metalloid, X is halide and "m" is an integer equal to the highest oxidation state of M. The homogenous fluid medium is maintained at a temperature sufficient to prevent precipitation of the catalyst complex from solution therein.

The Invention Processes

The invention catalyst may be utilized in the alkylation of isomerized alkanes with olefins.

The alkylation reaction is exothermic. Consequently, heat removal capability is a factor in reactor design selection.

Liquid Phase Operation

In this mode of operation the fluid of the reaction medium may comprise a mixture of n-alkane and iso-alkane, or just the isoalkane. The fluid may be used for forming a homogenous medium containing a desired quantity of dissolved catalyst complex by any of the procedures heretofore described and the medium then placed in a reaction zone where it is maintained at a temperature of at least about 50° F. (10° C.) while under a pressure of from about 250 to about 450 psia. Thereupon, contact of this medium with an olefin in a quantity to provide a mole ratio of alkane to olefin of from about 1 to about 10 will produce the alkylation reaction. Residence time of the medium and olefin within the reaction zone is preferably long enough to permit complete reaction of the quantity of olefin admitted to the zone. Preferably the residence time is at least 1 minute, more preferably at least about 4 minutes. Following the completion of reaction the hydrocarbon and catalyst content of the medium may be separated from each other by any technique as heretofore described.

An Embodiment of the Invention Alkylation Process Flow

The invention catalyst system may be utilized in any of a wide variety of process flow schemes in order to produce an alkylate product. Illustrative of the variety of process flows, is the simplified flow scheme illustrated in FIG. 1. In this flow scheme, fresh alkane 102 combines with a compressed charge 104 comprising recycled butanes 100, to produce catalyst dissolver feed 106 which is charged to the catalyst dissolver 110. Also charged to the dissolver 110 is a controlled quantity of makeup catalyst via conduit 112.

Figure 1:
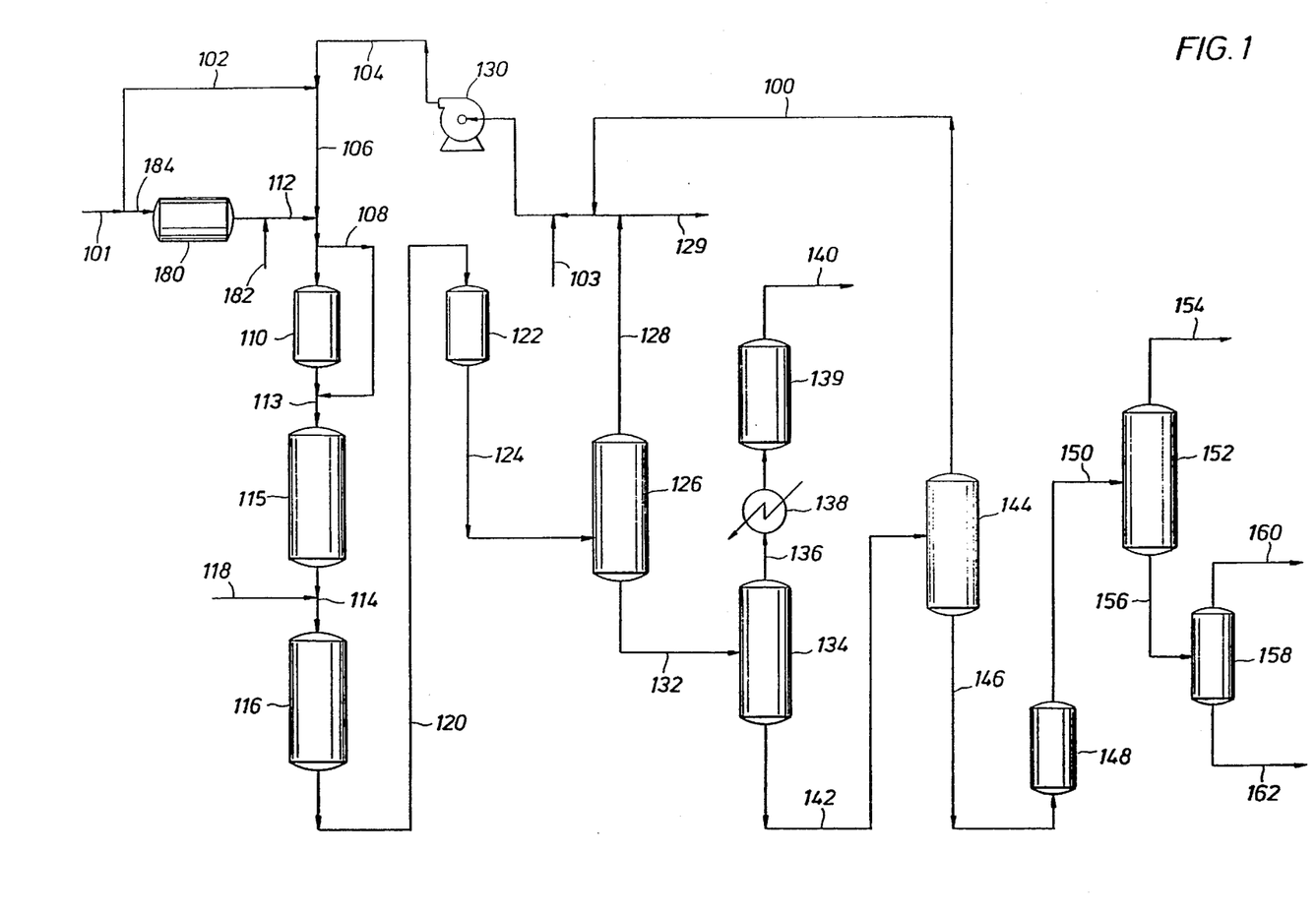
FIG. 1 is a flow diagram wherein the invention process is practiced under liquid phase conditions.

Make-up catalyst is produced in the "catalyst formation" or "make-up catalyst" reactor 180 which permits contact between an alkane/solvent stream 184 (shown as a slip stream taken from total fresh alkane charge 101) with the solid Lewis acid. To the stream 112 exiting reactor 180 is added a charge of Bronsted acid via line 182. This contacting step produces the invention catalyst which is soluble in the solvent. Further, the reactor 180 is a continuous flow reactor in that reactants and products flow through the reactor. It is designed for a residence time of less than about 5 minutes, preferably less than 3 minutes. Within these constraints, the reactor may be of any of a variety of designs. In one of the preferred designs, the reactor may be constructed like a conventional one tube pass shell and tube heat exchanger with the Lewis acid. Thus, the reactants will flow into the tube side of the reactor, flow along the tubes to allow dissolution of the Lewis acid. Alkane and catalyst flow from the exit end of the tubes into a collection header where the Bronsted acid is added and thence to dissolver 110. On the shell side of the catalyst formation reactor 180, a heat exchange fluid may be introduced in order to maintain the temperature within the desired operating range, since the catalyst formation reaction is exothermic.

The make-up catalyst provided via conduit 112 from the catalyst formation reactor 180 is sufficient to offset losses in the process and the formation reactor may be operated continuously or only intermittently, as needed.

Catalyst dissolver 110 contains discrete catalyst which has previously been recovered as a precipitate. This catalyst is dissolved into the fluid dissolver charge, which comprises the fluids in lines 106 and 112, up to the desired concentration of discrete catalyst relative to alkane. This may readily be achieved by bypassing a proportion of the charge via line 108 around the dissolver 110. The effluent from dissolver 110, now containing a useful amount of dissolved discrete catalyst, flows via conduit 113 to the alkylation reactor 116.

Conduit 113 flows into conduit 114 which is equipped with a T-piece one end of which is the inlet to an alkylation reactor 116 and the other end of which is connected to a line 118 which carries olefin feed for the alkylation reaction. As mentioned before, the olefinic feed component desirably comprises olefins having from 3 to about 9 carbon atoms.

The alkylation reactor 116 should be designed to provide a sufficient residence time for the alkylation reaction to take place to the desired level of isoalkane reaction. Within these constraints, the alkylation reactor could have any of a variety of designs. One example of such a design is a simple plug flow reactor which has the appropriate volume to provide the desired residence time and which has means for removing heat of reaction. Provisions should be made for addition of olefin at several points, preferably 3–5, along the length of the reactor. Thus, the reactor may comprise a conduit calculated to provide the appropriate residence time at design flow rates. Alternative designs, including one or more stirred vessels in series are also possible.

The effluent from the alkylation reactor 116 is led by a pipeline 120 to the inlet of a catalyst "adsorber" 122. This vessel is desirably of the same configuration as the catalyst dissolver 110. Thus, the charge to the precipitator is passed through the tubes containing an adsorbent for the catalyst. Under appropriate conditions of temperature and pressure, the catalyst adsorbs in adsorber 122. Thus, catalyst contained in "dissolver" 110 is gradually transferred to "adsorber" 122. When the catalyst is substantially exhausted from dissolver 110, the flow through the process system may be reversed by suitable piping, valving and control design so that vessel 122 becomes the "dissolver" while vessel 110 becomes the "adsorber."

The effluent from adsorber 122, which is essentially free of catalyst, is charged via line 124 to a depropanizer 134. This depropanizer distillation column 134 separates light ends, in particular propane and propene, from the alkylate and unreacted alkanes and olefins. The propane-propene stream is removed in the depropanizer overheads via line 136, is cooled and condensed in cooler-condenser 138, and to a receiver 139 from which it flows to a caustic scrubber via line 140 for the removal of any residual trace amounts of acid. The effluent from the caustic scrubber, now free of residual acid, may be used in other chemical processes or as a source of fuel. The bottom product 142 of depropanizer 134 is charged to a debutanizer 144 which removes butanes as an overhead product in line 100 for charging to the suction of pump 130 and thence recycled to the front end of the process via line 104. The bottom product 146 of the debutanizer 144 is treated to remove any residual acid in scrubber 148. The essentially acid-free effluent from caustic scrubber 148 is charged by line 150 to an alkylate splitter 152. The alkylate splitter separates the alkylate stream into a light alkylate overhead product 154 and a heavy alkylate bottom product 156. The heavy alkylate product 156 is then optionally charged to a alkylate flash drum 158 for separation into an overhead heavy alkylate 160 and a heavy tower bottom product 162.

The light alkylate stream 154 and the heavy alkylate product 160 are readily blended into gasoline, providing a high octane blending component that may be substituted for aromatic components.

While the simplified flow diagram of FIG. 1 shows the basic flow scheme, those of ordinary skill in the art will readily appreciate the additional equipment and modifications that may be necessary in practice.

As explained above, the invention catalyst and process may be carried out in any one of a variety of reactor designs. The reactor design is essentially only restricted by the functions that it is required to perform. For example, the reactor should be capable of withstanding reaction conditions. The design is desirably of a type that permits ease of removal of heat of reaction and the shell and tube reactor fulfills these needs.

Figure 2:
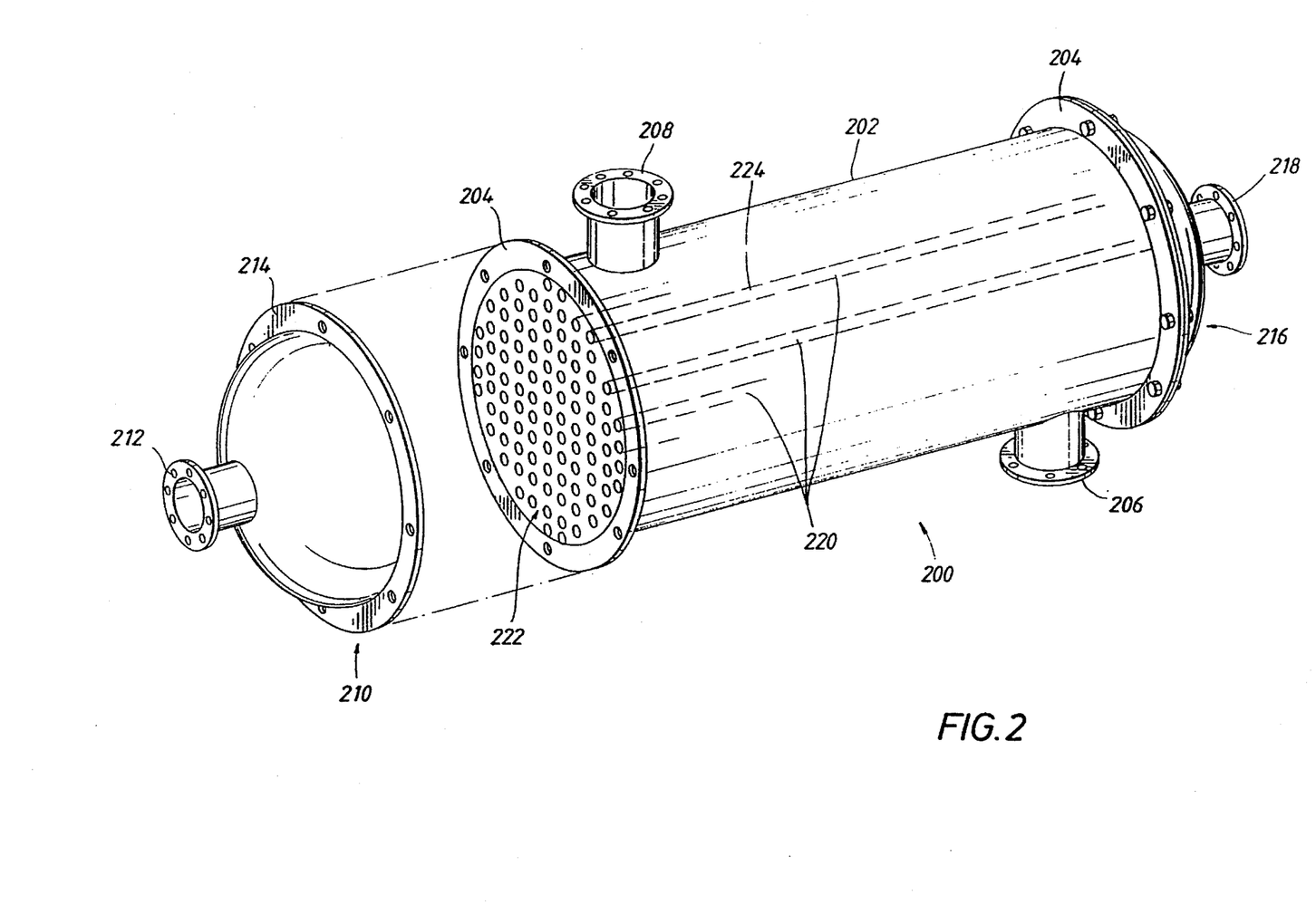
FIG. 2 is a schematic representation of a reactor useful in the invention process.

FIG. 2 illustrates, schematically, a reactor of the shell-and-tube-type design. The reactor 200 has a cylindrical shell 202 with flanges 204 at each end. Further, the shell is fitted with an inlet port 206 and an outlet port 208 for allowing a heat exchange fluid to travel through the shell of the reactor 200. Thus, the space within the shell surrounding the tubes provides a means for heat exchanging the tubes. An inlet bonnet 210 fitted with an inlet port 212, for receiving a charge of reactants, and a flange 214 is bolted to the flange 204. Similarly, an exit bonnet 216 is bolted to flange 204 at the exit end of the shell and is supplied with an exit port 218, for discharging reaction products from the reactor. The shell 202 contains a tube bundle 220. This tube bundle has an inlet header plate 222 through which tubes 224 extend and connect with exit header. The headers fit tightly within the shell so that a supercritical fluid cannot pass from the tube side to the shell side, or vice versa.

In practice, to produce a catalyst formation reactor, the tubes would be filled with a Lewis acid or a packing with Lewis acid distributed upon its surface. The reactor charge would enter at the inlet port 212, flow through the tube bundle 224, thereby contacting the Lewis acid and forming the catalyst, before exiting via exit port 218. At the same time, a coolant fluid would be charged through inlet port 206, flow over the tube bundle, thereby removing the exothermic heat of catalyst formation, and exit via exit port 208.

As explained, the reactor may also be used to dissolve the catalyst into a fluid stream or remove the catalyst from an alkylate stream onto the inner surface of the tubes or onto an adsorbent packing placed within the tubes. In this manner, the vessel functions as either a "dissolver" or a "adsorber" vessel.

To produce an alkylation reactor the tubes would not be filled with Lewis acid or with packing but would preferably be left empty to minimize pressure drop.

The following examples are illustrative of the invention and do not in any way limit or define the scope of the invention.

EXAMPLE 1

Liquid Phase Alkylation Procedure

All the catalyst preparation steps are conducted under a dry nitrogen atmospheres.

A 250 mL 3-necked round-bottom flask is equipped with a magnetic stirring bar, dropping funnel, water-cooled condenser, a thermometer, and under a positive nitrogen atmosphere. Place 9.7 g of di-isobutylaluminum chloride in the dropping funnel. Place 7.9 g of aluminum chloride and 200 ml (132 g) dried n-hexane in the round-bottom flask. Slowly add the diisobutylaluminum chloride to the flask with stirring. Allow the mixture to be stirred for 24 hours. The mixture is filtered with a pressurized filter. The filtrate is analyzed for aluminum content. Aluminum analysis: 1.8%, experimental: 1.9% theoretical. The n-hexane solution contains about 10.3% monoisobutyl-aluminum dichloride (MIBAD) catalyst precursor.

An i-butane feed consisting of 0.14 wt % of 1-chlorobutane was fed into the reactor unit at a rate of 96 cc/hr. A separate i-butane blend consisting of 2.5 wt % i-butyl AlCl$_2$ and 22.5 wt % n-hexane was fed at a rate of 7.8 cc/hr and mixed with the other stream at the operating conditions of 220° F. (104° C.) and 650 psig.

2-butene was added to this stream at a rate of 4.5 cc/hr. The total feed stream passed through a 4 foot long ¼ inch OD reactor tube before depressuring across a metering valve. The residence time is about 10 minutes. The concentration of the catalyst in the entire stream was 1550 wppm expressed as AlCl$_3$. Analysis of the exit stream showed 100% olefin conversion. The exit stream flowed into a coldtrap at −110° F. (−79° C.). The liquid collected in the coldtrap was allowed to warm to ice water temperature and the liquid was analyzed. The GC/MS analysis of the liquid is as follows:

|  | Wt % |
|---|---|
| propane | 1.1 |
| isobutane | 8.7 |
| n-butane | 0.3 |
| isopentane | 3.4 |
| 2,3-dimethylbutane | 4.6 |
| 2-methylpentane | 3.6 |
| 3-methylpentane | 0.4 |
| n-hexane | 14.9 |
| (from the catalyst blend) |  |
| 2,4-dimethylpentane | 4.3 |
| 2,3-dimethylpentane | 2.1 |
| 2,2,4-trimethylpentane | 11.5 |
| 2,5-dimethylhexane | 6.0 |
| 2,4-dimethylhexane | 4.8 |
| 2,3,4-trimethylpentane | 6.9 |
| 2,3,3-trimethylpentane | 4.0 |
| 2,3-dimethylhexane | 3.1 |
| 2,-methylheptane | 1.6 |
| 3-methylheptane | 1.0 |
| 2,2,5-trimethylhexane | 4.0 |
| 2,3,5-trimethylhexane | 1.5 |
| n-nonane (internal standard) | 10.4 |
| unidentified hydrocarbon | balance |

EXAMPLE 2

Liquid Phase Alkylation Using a Tubular Reactor (120° F.)

The operating procedure was generally as described in Example 1 except that the reaction was conducted at 120° F. instead of 220° F. to explore the effect of temperature on product distribution. The operating conditions were as follows: T=120° F., P=649 psig, 2-butene feedstock, i-butane/2-butene molar ratio=43, 2-butene/monoisobutylaluminum dichloride (MIBAD) molar ratio=82.4, 1-chlorobutane/MIBAD=1.4, residence time of 8.2 minutes. 100% olefin conversion was observed. The product was analyzed by gas chromotagraph as shown in the table below.

| COMPOUND | WT % (GC) |
|---|---|
| i-pentane | 3.2 |
| 2,3-dimethylbutane (DMB) | 5.1 |
| 2-methylpentane (MP) | .9 |
| 3-methylpentane | .4 |
| 2,4-dimethylpentane (DMP) | 4.1 |
| 2,2,3-trimethylbutane (TMB) | .6 |
| 2,3-dimethylpentane | 1.8 |
| 3-methylhexane (MH) | .3 |
| 2,2,4-trimethylpentane (TMP) | 26.9 |
| 2,5-dimethylhexane (DMH) | 3.9 |
| 2,2,3-TMP | 3.3 |
| 2,4-DMH | 3.3 |
| 2,3,4-TMP | 14.8 |
| 2,3,3-TMP | 9.8 |
| 2,3-Dk4H | 5.9 |
| 2-methylheptane (MHEP) | .9 |
| 3,4-DMH | 1.0 |
| 3-MHEP | .7 |
| 4-MHEP | .5 |
| 2,2,5-trimethylhexane (TMH) | 4.2 |

| COMPOUND | WT % (GC) |
|---|---|
| Other $C_9$ | 3.3 |
| $C_{10+}$ | 4.2 |

The Research Octane Number was calculated by a standard industrial approach modeled after the method of Hutson and Logan *Hydrocarbon Processing*, September, 1975. The approach uses weight percent of each component to calculate the contribution of that component to calculated octane (not mole percent as used by Logan and Hutson). The residual octane of all unidentified compounds is assumed to be 87 (as compared to 74 in the Logan and Hutson calculation). The Research Octane Number calculated by this method was 92.3. The Bromine Number was determined to be 2.7 indicating that the product was highly paraffinic. The product of Example 2 is clearly superior to that in Example 1 as witnessed by the presence of more of the desired TMP's and by the reduced amount of $C_{10+}$. This illustrates the benefit of low temperature operation.

EXAMPLE 3

Liquid Phase Alkylation Using a Tubular Reactor (110° and 100° F.)

Having made an improved product at 120° F., attempts were made to alkylate at 110° F. and at 100° F. The operating procedure was generally as described in Example 1. The operating conditions for the two tests are shown below:

| CONDITION | TEST-A | TEST-B |
|---|---|---|
| Temperature (°F.) | 110 | 103 |
| Pressure (psig) | 650 | 640 |
| Feedstock | 2-butene | 2-butene |
| i-butane/2-butene (molar) | 38.4 | 39.8 |
| 2-butene/MIBAD (molar) | 72 | 69 |
| 1-chlorobutane/MIBAD (molar) | 1.0 | 1.0 |
| holding time (min.) | 7.0 | 9.1 |

In Test-A, 100% olefin conversion was observed. 81% olefin conversion was noted in Test-B. The product was collected in a cold trap in a dry ice/acetone bath. Unconverted i-butane was removed and the alkylate was analyzed by gas chromatography. The analysis is summarized in the table below.

| | WT % (GC) | |
|---|---|---|
| CONDITION | TEST-A | TEST-B |
| i-pentane | 1.4 | 1.4 |
| 2,3-DMB | 3.5 | 3.5 |
| 2-MP | .3 | .3 |
| 3-MP | .2 | .2 |
| n-$C_6$ | .3 | .3 |
| Other $C_6$ | .1 | .1 |
| 2,4-DMP | 2.2 | 2.2 |
| 2,2,3-TMB | .7 | .7 |
| 2,3-DMP | 1.7 | 1.7 |
| 3-MH | .1 | .1 |
| 2,2,4-TMP | 20.7 | 20.6 |
| 2,5-DMH | 1.4 | 1.4 |
| 2,4-DMH | 1.6 | 1.6 |
| 2,2,4-TMP | 1.6 | 1.6 |
| 2,3,4-TMP | 17.4 | 17.4 |
| 2,3,3-TMP | 10.6 | 10.6 |
| 2,3-DMH | 2.0 | 2.0 |
| 2-MHEP | .3 | .3 |
| 3,4-DMH | .4 | .4 |
| 3-MHEP | .4 | .4 |
| Other $C_8$ | 1.8 | 1.9 |
| 2,2,5-TMH | 4.6 | 4.5 |
| Other $C_9$ | 7.9 | 7.9 |
| $C_{10+}$ | 18.7 | 18.8 |

Octane numbers were calculated for both tests using the procedure described in Example 2. In accordance with the similarity in product analyses the calculated octane number for Test-A was 93.9 and that for Test-B was 94.0. The Bromine Number for Test-A was 19; that for Text B was 28, indicating significant amounts of unsaturation in the $C_{10+}$ fraction. Comparing Examples 2 and 3, product octane is improved by reducing temperature below 120° F. However, the $C_{10+}$ yield increases and becomes more olefinic.

EXAMPLE 4

Butadiene Effect on Tubular Reactor Performance (120° F.)

Butadiene is a common impurity in alkylation feeds which is produced as a byproduct in catalytic cracking. In conventional alkylation processes butadiene concentration is typically limited to 1000–2000 ppm (relative to total olefins) because it polymerizes and reacts with the alkylation catalyst to form an acid-soluble oil. *Hydrocarbon Processing*, November, 1991, pp. 89–92.

To test the effect of butadiene on reactor performance using the soluble catalysts of this process, 6600 ppm of 1,3-butadiene was blended with 2-butene feed. The resultant feed was tested in the tubular reactor at conditions similar to those used in Example 2. The operating conditions, product analyses obtained by gas chromatograph and calculated octane numbers are summarized in the table below. Octane numbers (RON) were calculated by the procedure outlined in Example 2. 100% olefin conversion was observed in both tests.

| TEST | EXAMPLE 5 | EXAMPLE 4 |
|---|---|---|
| Olefin | 2-Butene | 2-Butene |
| Temperature (°F.) | 120 | 120 |
| Pressure (PSIG) | 650 | 650 |
| Residence Time (min.) | 8.2 | 6.5 |
| Olefin/Catalyst (mol/mol) | 80 | 80 |
| Activator/Catalyst (mol/mol) | 1.3 | 1.3 |
| 1-Butane/olefin | so | 40 |
| Bromine Number | 3 | 16.3 |
| Butadiene (MPPM in Olefin) | 0 | 6600 |
| Product Analysis (Wt %) | | |
| iso-Pentane | 3.2 | 4.3 |
| 2,3-DMP | 5.1 | 6.8 |
| 2-MP | .9 | .6 |
| 3-MP | .4 | |
| N-$C_6$ | .3 | |
| Other $C_6$ | .2 | |
| 2,4-DMP | 4.1 | 4.8 |
| 2,2,3-TMB | .6 | .7 |
| 2,3-DMP | 1.8 | 2.2 |
| 3-MH | .3 | |
| Other $C_7$ | .5 | |
| 2,2,4-TMP | 26.9 | 26.8 |
| 2,5-DMH | 3.9 | 2.3 |
| 2,4-DMH | 3.3 | 1.7 |

-continued

| TEST | EXAMPLE 5 | EXAMPLE 4 |
|---|---|---|
| 2,2,3-TMP | 3.3 | 1.7 |
| 2,3,4-TMP | 14.8 | 17.4 |
| 2,3,3-TMP | 9.8 | 9.6 |
| 2,3-DMH | 5.9 | 1.8 |
| 2-M HEP | .9 | |
| 3,4-DMH | 1.0 | |
| 3-M HEP | .7 | |
| Other $C_8$ | .5 | |
| 2,2,5-TMH | 4.2 | 5.8 |
| Other $C_9$ | 3.3 | 4.6 |
| $C_{10+}$ | 4.2 | 7.9 |
| RON (calc) | 91.3 | 95.7 |
| TMP/DMH | 3.4 | 9.5 |

Butadiene increased the calculated octane number of the product by increasing the trimethylpentanes and decreasing the dimethylehexanes. Butadiene also resulted in an increase in the production of unsaturated $C_{10+}$ as shown by the increase in Bromine Number and $C_{10+}$ in the product of Example 4 relative to Example 2.

EXAMPLE 5

Liquid Phase Alkylation Using a Well-Stirred Reactor (120° F.)

A catalyst preparation step and experimental operating procedure similar to Example 1 were used except that the tubular reactor was replaced by a flat-bottom stirred reactor of 75 cc total volume. Alkylation was conducted by feeding i-butane, catalyst and 2-butene at the bottom of the reactor. Product was removed at the top of the reactor and collected in a cold trap chilled with dry ice/acetone. Unreacted i-butane was removed and the alkylate was analyzed by gas chromatograph. The operating conditions product analyses and calculated octane number are summarized in the table below. Research octane number (RON) was calculated by the procedure outlined in Example 2. 100% olefin conversion was observed in the test.

| Alkylation in Stirred Reactor | |
|---|---|
| Test | Example 5 |
| Olefin | 2-Butene |
| Temperature (°F.) | 120 |
| Pressure (PSIG) | 647 |
| Residence Time (min) | 21 |
| Olefin/Catalyst (mol/mol) | 63 |
| Activator/Catalyst (mol/mol) | 1.2 |
| i-Butane/Olefin (mol/mol) | 28 |
| Bromine No. | 1 |
| Product Analysis (Wt %) | |
| i-pentane | 2.5 |
| 2,3-DMB | 2.8 |
| 2-MP | .4 |
| 3-MP | .2 |
| n-$C_6$ | .1 |
| 2,4-DMP | 3.0 |
| 2,2,3-TMB | 3.6 |
| 3,3-DMP | 2.2 |
| 3-MH | 2.9 |
| 2,3-DMP | 1.5 |
| Other $C_7$ | |
| 2,2,4-TMP | 35.2 |
| 2,5-DMH | 3.0 |
| 2,4-DMH | 2.7 |
| 2,2,3-TMP | 2.7 |
| 2,3,4-TMP | 15.5 |
| 2,3,3-TMP | 12.3 |

-continued

| Alkylation in Stirred Reactor | |
|---|---|
| Test | Example 5 |
| 2,3-DMH | 2.0 |
| 2-MHEP | .4 |
| 3,4-DMH | .4 |
| 3-MHEP | .4 |
| Other $C_8$ | .2 |
| 2,2,5-TMH | 3.0 |
| Other $C_9$ | 1.9 |
| $C_{10+}$ | 8.8 |
| RON (calc) | 95.1 |
| TMP/DMH | 8.1 |

The octane number reflects the percent of $C_8$ in the product as well as the relative amounts of TMP and DMH. The low Bromine Number indicates that the product is highly paraffinic.

EXAMPLE 6

Butadiene Effects on Alkylation in a Well-Stirred Reactor (120° F.)

A test similar to Example 5 was conducted in a stirred reactor having a cupped bottom in place of the flat bottom of Example 5. An alkylation test was conducted at conditions noted in the table below. A second test was conducted with the addition of 6600 molar ppm of 1,3-butadiene to the 2-butene feed. In both cases product was removed from the top of the reactor and collected in a cold trap chilled with dry ice/acetone. Unreacted i-butane was removed and the alkylate was analyzed by gas chromatograph. Operating conditions, product analyses and calculated octane numbers are summarized in the table below. Research octane number was calculated by the procedure outlined in Example 2. 100% olefin conversion was observed in the test.

| Alkylation in Stirred Reactor | | |
|---|---|---|
| TEST | TEST A | TEST B |
| Olefin | 2-Butene | 2-Butene |
| Temperature | 121 | 121 |
| Pressure (PSIG) | 645 | 645 |
| Residence Time (min) | 20 | 19 |
| Olefin/Catalyst (mol/mol) | 96 | 79 |
| Activator/Catalyst (mol/mol) | 1.2 | 1.3 |
| i-butane/olefin (mol/mol) | 20 | 22 |
| Butadiene (mppm in Olefin) | 0 | 6600 |
| Bromine No. | <1 | 4.3 |
| Product Analysis (Wt %) | | |
| i-pentane | 5.9 | 4.3 |
| 2,3-DMP | 3.5 | 4.5 |
| 2-HP | 1.8 | .7 |
| 3-MP | .8 | .3 |
| n-$C_6$ | .1 | |
| 2,4-DMP | 3.7 | 4.1 |
| 2,2,3-TMP | .5 | .5 |
| 3,3-DMP | 1.0 | .3 |
| 3-MH | .7 | .2 |
| 2,3-DMP | 1.9 | 1.8 |
| Other $C_7$ | | |
| 2,2,4-TMP | 32.8 | 35.7 |
| 2,5-DMH | 6.7 | 3.4 |
| 2,4-DMH | 6.0 | 3.2 |
| 2,2,4-TMP | 6.0 | 3.2 |
| 2,3,4-TMP | 5.6 | 12.4 |
| 2,3,3-TMP | 9.4 | 11.9 |
| 2,3-DMH | 2.3 | 2.0 |
| 2-MHEP | 1.5 | .5 |
| 3,4-DMH | .6 | .4 |

17
-continued

| Alkylation in Stirred Reactor | | |
|---|---|---|
| TEST | TEST A | TEST B |
| 3-MHEP | 1.0 | .4 |
| Other C$_8$ | .4 | |
| 2,2,5-TMH | 3.1 | 3.7 |
| Other C$_9$ | 1.5 | 1.7 |
| C$_{10+}$ | 3.0 | 5.0 |
| RON (calc) | 90.4 | 94.9 |
| TMP/DMH | 3.4 | 7 |

The octane number was higher during the test with butadiene addition. This resulted from an increase in C$_8$ in the product as well as from an increase in the amount of TMP produced relative to DMH. A minor increase in C$_{10+}$ and unsaturation as reflected by a slight increase in Bromine Number, were also noted during the butadiene test.

EXAMPLE 7

Liquid Phase Alkylation Using a Well-Stirred Reactor (77° F.)

Having demonstrated in Examples 2 and 3 that alkylation could be practiced at 100°–120° F., an attempt was made to conduct alkylation at room temperature. The apparatus, experimental operation, and octane calculation procedures are as described in Example 3. The operating conditions, product analyses and calculated octane number are summarized in the table below. 100% olefin conversion was observed throughout the test.

| Alkylation in Stirred Reactor | |
|---|---|
| Olefin | 2-butene |
| Temperature (°F.) | 77 |
| Pressure (PSIG) | 647 |
| Residence Time (min) | 19.3 |
| Olefin/Catalyst (mol/mol) | 49.6 |
| 1-Chlorobutane/MIBAD (molar) | .8 |
| i-Butane/Olefin (mol/mol) | 19.3 |
| Bromine No. | |
| Product Analysis (wt %) | |
| i-pentane | 3.6 |
| 2,3-DMB | 2.1 |
| 2-MP | .8 |
| 3-MP | .2 |
| n-C$_6$ | .8 |
| 2,4-DMP | 2.0 |
| 2,2,3-TMB | 1.4 |
| 2,3-DMP | .5 |
| 3-MH | .3 |
| 2,3-DMP | .9 |
| Other C$_7$ | |
| 2,2,4-TMP | 20.3 |
| 2,5-DMH | 3.1 |
| 2,4-DMH | 3.0 |
| 2,2,3-TMP | 3.0 |
| 2,3,4-TMP | 10.7 |
| 2,3,3-TMP | 6.9 |
| 2,3-DMH | 11.6 |
| 2-MHEP | 1.1 |
| 3,4-DMH | 1.2 |
| 3-MHEP | .9 |
| Other C$_8$ | .2 |
| 2,2,5-TMH | 3.9 |
| Other C$_9$ | 4.3 |
| C$_{10+}$ | 16.5 |
| RON (Calc) | 88.8 |
| TMP/DMH | 2.2 |

18

The above demonstrates that alkylation can be conducted at room temperature.

Although the invention has been described with reference to its preferred embodiments, those of ordinary skill in the art may, upon reading this disclosure, appreciate changes and modifications which do not depart from the scope and spirit of the invention as described above or claimed hereafter.

We claim:

1. A method for alkylating an olefin having at least three carbon atoms with an isoparaffin having at least four carbon atoms comprising the steps of:

first forming a Lewis acid-hydrocarbon complex catalyst comprising the product of reaction of at least (a) a Lewis acid of the formula $R_{(m-2-z)}MX_{(2+z)}$ wherein M is a Group 3a, 5a or 5b metal, X is a halide, R is a hydrocarbyl radical having 1 to 12 carbon atoms, "m" is an integer equal to the greatest oxidation state of M, and "z" is an integer of 0, 1 or m-2;

(b) a hydrogen halide; and (c) an organic compound selected from
(1) paraffins having 12 or fewer carbon atoms, or
(2) olefins having 12 or fewer carbon atoms, said product of reaction having the formula $[C_{at}]^+_a[R_{(m-2-z)}MX_{(2+z+a)}]^-$ wherein $C_{at}$ is a carbocation and "a" is a number greater than 0.5 and less than 2.5, and wherein "a" represents the molar ratios of hydrogen halide and the organic compound of the forming step relative to the Lewis acid; said product of reaction dissolved in a liquid second paraffin hydrocarbon to form a solution; wherein the concentration of said product of reaction is from about 3.0 to about 30 millimoles per 1,000 grams of said solution;

maintaining the solution containing the product of reaction dissolved in the liquid second paraffin hydrocarbon at a temperature such that the catalyst does not precipitate for a time sufficient for substantially complete conversion to alkylated product to occur in said solution;

next adding the hydrocarbon to be alkylated prior to any substantial precipitation of the catalyst to yield alkylated product hydrocarbon; and then separating the alkylated product isoparaffin from the Lewis acid-hydrocarbon complex catalyst;

wherein the second paraffin is an iso-alkane having from 4 to 12 carbon atoms and the hydrocarbon to be alkylated is an olefin having from 3 to 5 carbon atoms, said solution and olefin being maintained at a temperature of from about 10° to about 10° C. and under a pressure sufficient to maintain said solution and olefin in a liquid state and the product isoparaffin comprises branched hydrocarbon compounds having a greater number of carbon atoms than either of the iso-alkane or olefin.

2. The method of claim 1 wherein the Lewis acid is of the formula $R_{(m-2-z)} AlX_{2+z}$ and X is chloride and the hydrogen halide is HCl.

3. The method of claim 2, wherein the Lewis acid is $R_{1-z}AlCl_{2+z}$ and the hydrogen halide is HCl.

4. The method of claim 2, wherein the Lewis acid is AlCl$_3$ or isobutylaluminum dichloride.

5. The process of claim 1, wherein the isoalkane is isobutane.

6. The process of claim 5, wherein said solution is maintained at a temperature of from about 38° to about 83° C.

7. The process of claim 6, wherein said solution is maintained at a temperature of from about 38° to about 71° C.

8. The process of claim 6, wherein the olefin is a butene.

9. The process of claim 5, wherein the Lewis acid is of the formula $R_{(m-2-z)} AlX_{2+z}$ and X is chloride or bromide and the hydrogen halide is HCl or HBr.

10. The process of claim 9, wherein the Lewis acid is $R_{1-z}AlCl_{2+z}$ and the hydrogen halide is HCl.

11. The process of claim 10 wherein the Lewis acid is $AlCl_3$ or isobutylaluminum dichloride.

12. The process of claim 9, wherein the isoalkane is isobutane and the olefin is a butene.

13. The process of claim 1, wherein the olefin is 2-butene.

14. The process of claim 12, wherein said solution is maintained at a temperature of from about 38° to about 83° C.

15. The process of claim 14, wherein said solution is maintained at a temperature of from about 38° to about 71° C.

16. The process of claim 1, wherein butadiene is present in said solution in a concentration of up to about 1.5 times the concentration of the catalyst.

17. The method of claim 1 wherein the Lewis acid is of the formula $R_{(m-2-z)} AlX_{2+z}$ and X is bromide and the hydrogen halide is HBr.

18. A method for alkylating an olefin having at least three carbon atoms with an isoparaffin having at least four carbon atoms comprising the steps of:

first forming a Lewis acid-hydrocarbon complex catalyst consisting essentially of:

a Lewis acid hydrocarbon complex of the formula:

$[C_{at}]^+_a[R_{(m-2-z)}MX_{(2+z+a)}]^-$ wherein $C_{at}$ is a carbocation, M is a Group 3a, 5a or 5b metal, X is a halide, R is a hydrocarbyl radical having 1 to 12 carbon atoms, "m" is an integer equal to the greatest oxidation state of M, "z" is an integer of 0, 1 or m-2, and "a" is a number greater than 0.5 and less than 2.5; said catalyst dissolved in a liquid paraffin hydrocarbon to form a solution;

maintaining the solution containing the catalyst dissolved in the liquid paraffin hydrocarbon at a temperature such that the catalyst does not precipitate for a time sufficient for substantially complete conversion to alkylated product to occur in said solution;

next adding the hydrocarbon to be alkylated prior to arty substantial precipitation of the catalyst to yield alkylated product hydrocarbon; and then separating the alkylated product isoparaffin from the Lewis acid-hydrocarbon complex catalyst;

wherein the paraffin is an iso-alkane having from 4 to 12 carbon atoms and the hydrocarbon to be alkylated is an olefin having from 3 to 5 carbon atoms, said solution and olefin being maintained at a temperature of from about 10° to about 105° C. and under a pressure sufficient to maintain said solution and olefin in a liquid state and the product isoparaffin comprises branched hydrocarbon compounds having a greater number of carbon atoms than either of the iso-alkane or olefin.

19. The method of claim 18 wherein the catalyst is of the formula:

$$[C_4 H_9]^+[C_4H_9AlCl_3]^-$$

20. The method of claim 2 wherein the time for forming the Lewis acid complex is less than about 5 minutes.

21. The method of claim 4 wherein the time for forming the Lewis acid complex is less than about 5 minutes.

22. The method of claim 11 wherein the time for forming the Lewis acid complex is less than about 5 minutes.

* * * * *

UNITED STATES PATENT AND TRADEMARK OFFICE
CERTIFICATE OF CORRECTION

PATENT NO. : 5,510,561
DATED : April 23, 1996
INVENTOR(S) : Larry G. Sherman and William A. Yuill It is certified that error appears in the above-indentified patent and that said Letters Patent is hereby corrected as shown below:

Column 14, line 45, delete "Example 5" and insert
--Example 2--

Column 18, line 47, delete "about 10 to about 10°"
and insert --about 10 to about 105°--

Signed and Sealed this

Fourteenth Day of October, 1997

Attest:

BRUCE LEHMAN

*Attesting Officer*  *Commissioner of Patents and Trademarks*